(12) United States Patent
Roehrig et al.

(10) Patent No.: US 7,809,175 B2
(45) Date of Patent: Oct. 5, 2010

(54) DISPLAYING AND NAVIGATING COMPUTER-AIDED DETECTION RESULTS ON A REVIEW WORKSTATION

(75) Inventors: Jimmy R. Roehrig, Aptos, CA (US); Julian Marshall, Los Altos, CA (US)

(73) Assignee: Hologic, Inc., Marlborough, MA (US)

( * ) Notice: Subject to any disclaimer, the term of this patent is extended or adjusted under 35 U.S.C. 154(b) by 1288 days.

(21) Appl. No.: 11/173,960

(22) Filed: Jul. 1, 2005

(65) Prior Publication Data
US 2007/0003119 A1    Jan. 4, 2007

(51) Int. Cl.
*G06K 9/00* (2006.01)

(52) U.S. Cl. .................... 382/128; 715/700; 715/763
(58) Field of Classification Search .................. None
See application file for complete search history.

(56) References Cited

U.S. PATENT DOCUMENTS

| | | | |
|---|---|---|---|
| 5,987,345 A | 11/1999 | Engelmann et al. | |
| 6,266,435 B1 * | 7/2001 | Wang | 382/132 |
| 6,434,262 B2 | 8/2002 | Wang | |
| 2001/0043729 A1 | 11/2001 | Giger et al. | |
| 2002/0193676 A1 | 12/2002 | Bodicker et al. | |
| 2004/0100476 A1 | 5/2004 | Morita et al. | |
| 2004/0184644 A1 | 9/2004 | Leichter et al. | |
| 2007/0019849 A1 * | 1/2007 | Kaufman et al. | 382/128 |

* cited by examiner

*Primary Examiner*—Vu Le
*Assistant Examiner*—Claire Wang
(74) *Attorney, Agent, or Firm*—Brian J. Daiuto

(57) ABSTRACT

Display and navigation for multiple computer-aided detection (CAD) detections is described. A medical image is displayed to a viewer, and a request is received to instantiate CAD-assisted viewing. A timewise presentation sequence for the CAD detections is automatically computed according to a predetermined sequencing criterion. For each CAD detection, an expanded presentation window is displayed for its associated location in the medical image, the expanded presentation windows being displayed according to the timewise presentation sequence. Also described is a navigational tool comprising a plot of an operating curve onto which a computed feature associated with the CAD algorithm can be mapped, the operating curve characterizing an application of the CAD algorithm to a reference database of mammographic cases having known diagnoses. The navigational tool further comprises a plurality of CAD pointer icons spatially distributed therealong according to mappings of the computed feature for the CAD detections onto the operating curve.

25 Claims, 11 Drawing Sheets

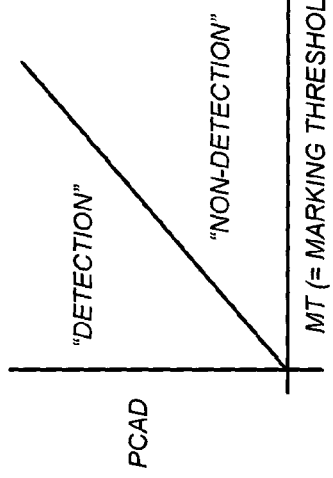
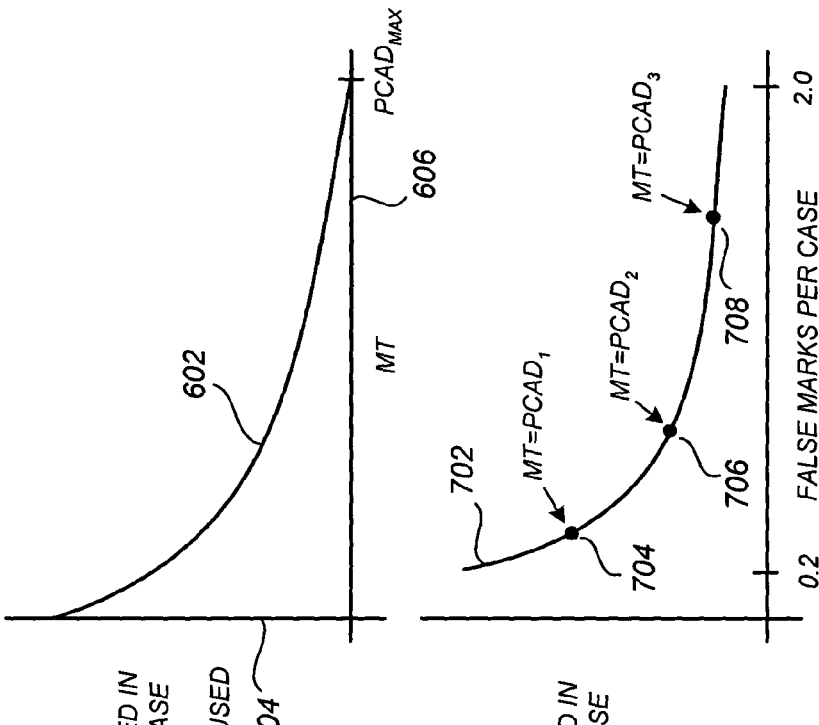
FIG. 5
FIG. 6
FIG. 7

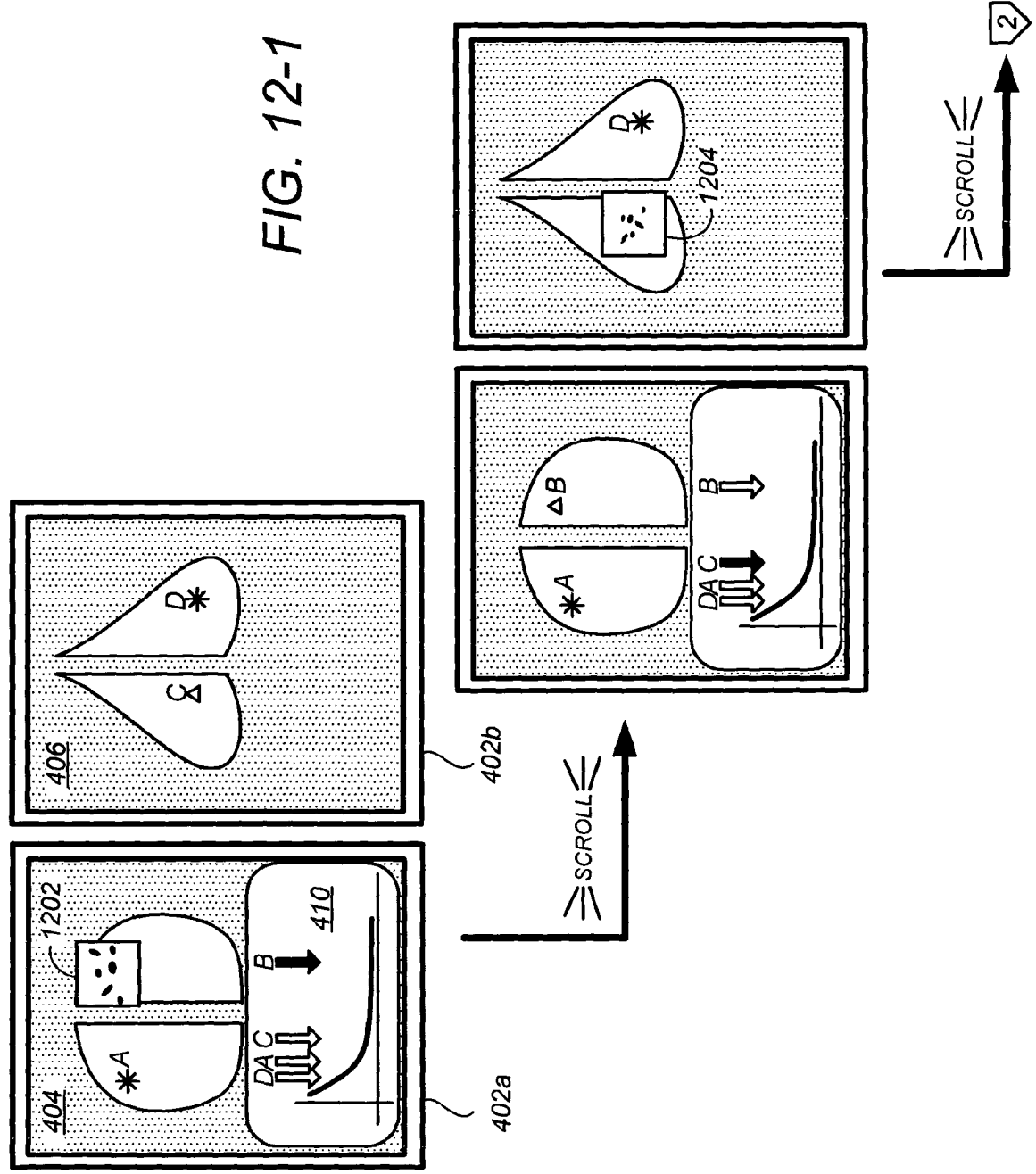

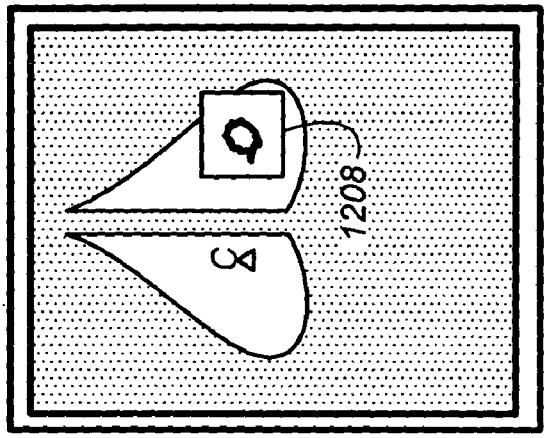
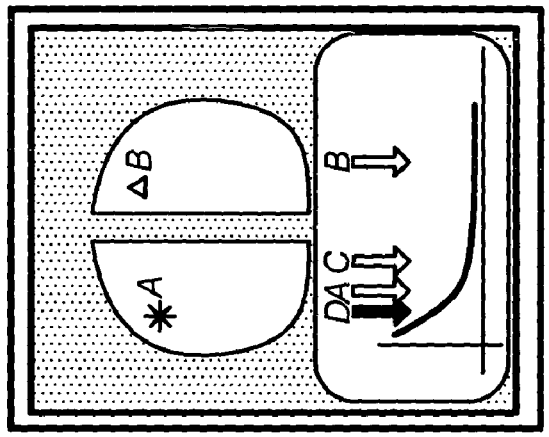
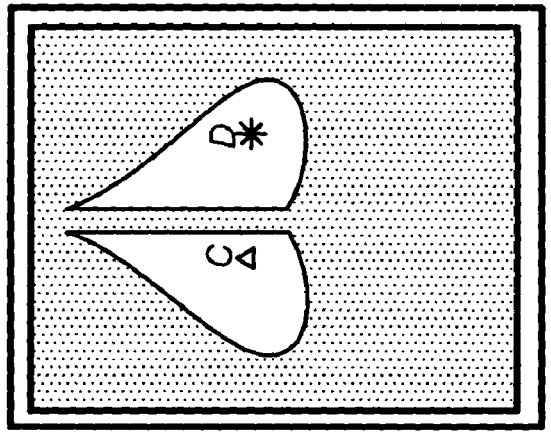
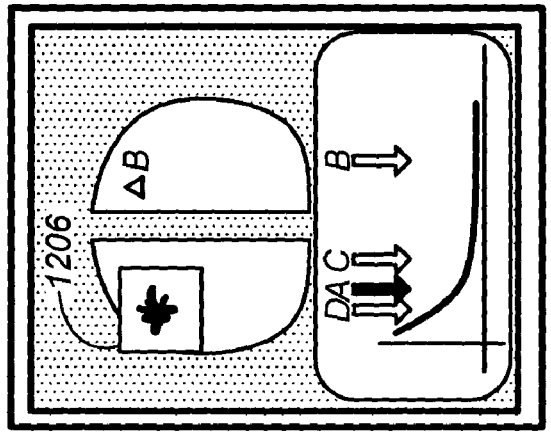
FIG. 12-2

DISPLAYING AND NAVIGATING COMPUTER-AIDED DETECTION RESULTS ON A REVIEW WORKSTATION

FIELD

This patent specification relates to the computer-aided detection of abnormalities in medical images. More particularly, this patent specification relates to displaying and navigating computer-aided detection results on a review workstation.

BACKGROUND

Computer-aided detection (CAD) generally refers to the use of computers to analyze medical images to detect anatomical abnormalities therein. Sometimes used interchangeably with the term computer-aided detection are the terms computer-aided diagnosis, computer-assisted diagnosis, or computer-assisted detection. As used herein, CAD detection refers to a location in a medical image that a CAD system, in accordance with a CAD algorithm operating on the medical image, has identified as warranting some type of attention by a radiologist. As used herein, radiologist generically refers to a medical professional that analyzes medical images and makes clinical determinations therefrom, it being understood that such person might be titled differently, or might have differing qualifications, depending on the country or locality of their particular medical environment.

As known in the art, a CAD algorithm usually identifies a preliminary set of candidate detections in a medical image and then selects which ones, if any, will qualify as actual CAD detections based on a variety of computed features associated with the candidate detections. The CAD results, i.e., the body of information associated with the operation of the CAD algorithm on the medical image, are most often communicated in the form of annotation maps comprising graphical annotations (CAD markers) overlaid on a diagnostic-quality or reduced-resolution version of the medical image, one CAD marker for each CAD detection.

CAD results are mainly used by radiologists as "secondary reads" or secondary diagnosis tools. When analyzing a medical image, the radiologist usually makes his or her own analytical determinations before looking at the CAD results, which either verify those determinations or trigger further inspection of the image. Some CAD implementations have used CAD results in a "concurrent reading" context in which the radiologists look at the CAD results at the same time that they look at the images.

In the field of x-ray mammography, thousands of mammography CAD systems are now installed worldwide, and are used to assist radiologists in the interpretation of millions of mammograms per year. Mammography CAD systems are described, for example, in U.S. Pat. No. 5,729,620, U.S. Pat. No. 5,815,591, U.S. Pat. No. 5,917,929, U.S. Pat. No. 6,075,879, U.S. Pat. No. 6,266,435, U.S. Pat. No. 6,434,262, and U.S. 2001/0043729A1, each of which is incorporated by reference herein. Mammography CAD algorithms analyze digital or digitized images of standard mammographic views (e.g. CC, MLO) for characteristics commonly associated with breast cancer, such as calcifications, masses, and architectural distortions. It is to be appreciated that although presented in the particular context of x-ray mammography, the preferred embodiments described herein are applicable for a variety of medical imaging modalities such as computerized tomography (CT) imaging, magnetic resonance imaging (MRI), positron emission tomography (PET), single-photon emission computed tomography (SPECT), and ultrasound, and even less conventional medical imaging modalities such as thermography, electrical conductivity-based modalities, and the like.

Substantial effort and attention has been directed to increasing the analysis capabilities of CAD systems, resulting in ever-increasing amounts of information that is available to the radiologist for review. By way of example, U.S. Pat. No. 6,434,262, supra, describes providing enhanced image tiles for each CAD detection including close-up viewing capabilities. In another example, U.S. Pat. No. 6,266,435, supra, describes providing numerical characterizations adjacent to each CAD detection such as probabilities or other predictive values, describes analog representations of such characterizations within the CAD markers themselves (e.g., shape, size, color), and describes displaying different sets of CAD markers for different thresholds that may even be user-selectable. By way of still example, U.S. 2001/0043729A1, supra, discusses a search workstation in which the display shows both a computer classification output for a lesion as well as images of lesions from other medical images with known diagnoses based on a similarity of computer-extracted features.

Problems can arise, however, at the interface between (a) the amount of information available to the radiologist, and (b) the amount of information that can be usefully perceived by the radiologist in a reasonable amount of time. These issues are especially important in today's radiology environment, where there is a ongoing tension between providing high-quality detection/diagnosis for each patient and maintaining adequate patient throughput to keep costs under control. A large body of information associated with a medical image would have substantially diminished value if the radiologist does not have the time or inclination to view that information. In an almost-humorous reflection of this situation, U.S. 2004/0223633A1 discusses automatically inserting false, misleading CAD markers in medical images to ensure that the radiologist, knowing that one of the marks might be false, will perform a more thorough review. Other issues arise as would be apparent to one skilled in the art upon reading the present disclosure.

Accordingly, it would be desirable to provide a medical review workstation that provides a judicious selection of helpful information to the radiologist for assisting in the screening and/or diagnosis of a medical image.

It would be further desirable to facilitate quick yet contextually meaningful navigation among multiple CAD detections in a medical image.

It would be still further desirable to provide, in the context of multiple CAD detections for a medical image, a tool for quickly perceiving characteristics of those CAD detections relative to each other.

It would be even further desirable to provide such tools in a manner that seamlessly integrates into existing radiology workflows.

SUMMARY

A method for displaying a plurality of CAD detections associated with a mammographic case is provided, the mammographic case comprising a plurality of mammographic images, each CAD detection being associated with a location in one of the mammographic images. A plurality of the mammographic images are displayed to the viewer. A request is received from the viewer to instantiate CAD-assisted viewing of the mammographic case. A timewise presentation sequence for the CAD detections is automatically computed according to a predetermined sequencing criterion. For each CAD detection, an expanded presentation window is displayed for its associated location in the associated mammographic image. The expanded presentation windows are sequentially displayed according to the computed timewise presentation sequence for the CAD detections.

In one preferred embodiment, the predetermined sequencing criterion is based on a scalar overall probability metric that, as part of the CAD algorithm, is thresholded for qualifying candidate detections as becoming "detections" versus "non-detections". In another preferred embodiment, the predetermined sequencing criterion is based on a different computed feature or combinations of different computed features, such as mass area metrics, edge roughness metrics, number of calcifications in cluster metrics, spiculatedness metrics, etc. In another preferred embodiment, the predetermined sequencing criterion is viewer-selectable.

According to another preferred embodiment, a navigational tool is provided in general proximity to the mammographic images. The navigational tool comprises a plot of an operating curve onto which a first computed feature associated with the CAD algorithm can be mapped, the operating curve characterizing an application of the CAD algorithm to a reference database of mammographic cases having known diagnoses. The navigational tool further comprises a plurality of CAD pointer icons corresponding respectively to each of the CAD detections, the CAD pointer icons being spatially distributed along the navigational tool according to the mappings of the first computed feature of the corresponding CAD detections onto the operating curve. Viewer perception of the multiple CAD detections relative to each other and to the reference database with respect to that first computed feature characteristic is facilitated. Navigation from one expanded presentation window to the next is based on the spatial order of the CAD pointer icons on the navigational tool. Alternatively or in conjunction therewith, navigation to an expanded presentation window for a particular CAD detection is achieved by user selection of a particular CAD pointer icon on the navigational tool.

BRIEF DESCRIPTION OF THE DRAWINGS

FIG. 5 illustrates a thresholding rule in a CAD algorithm according to a preferred embodiment;

FIGS. 6-9 illustrate operating curves of a navigational tool according to one or more of the preferred embodiments;

FIG. 12 illustrates navigating CAD results using a navigational tool according to a preferred embodiment;

DETAILED DESCRIPTION

Figure 1:
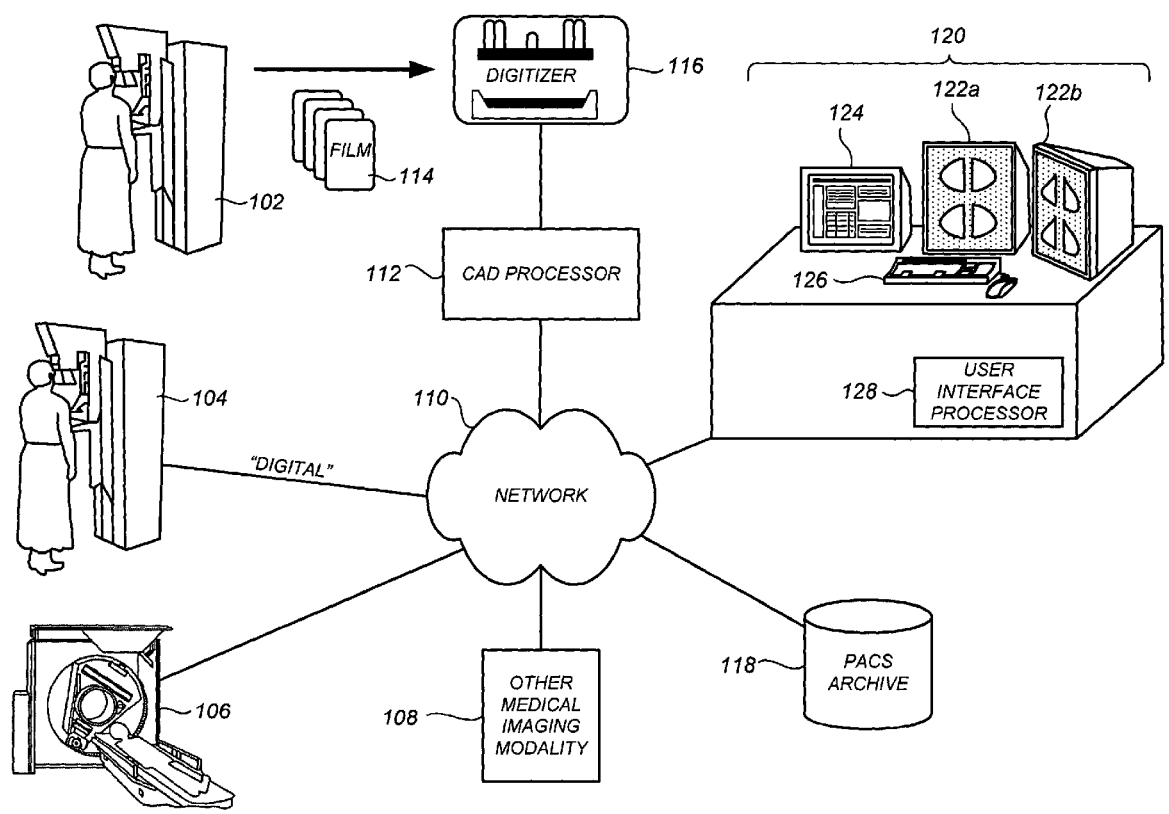
FIG. 1 illustrates a conceptual diagram of a medical imaging environment including a softcopy workstation according to a preferred embodiment.

FIG. 1 illustrates a conceptual diagram of a medical imaging environment for which one or more of the preferred embodiments is particularly suited. Shown in FIG. 1 is a network 110, which may be a HIS/RIS (Hospital Information System/Radiology Information System) network, to which is coupled a film mammogram acquisition device 102, a digital mammogram acquisition device 104, a computed tomography (CT) acquisition device 106, and a generalized "other" medical imaging device 108. A CAD processor 112 coupled to the network 110 receives digital medical images from one or more of the devices 104-108, and/or from a digitizer 116 that digitizes x-ray mammogram films 114 generated by the film mammogram acquisition device 102. Preferably, the various medical images and related information are communicated according to the DICOM (Digital Imaging and Communications in Medicine) standard and the network 110 supports the TCP/IP protocol, which is used as the transport protocol for the DICOM standard.

The CAD processor 112 processes the medical images according to a CAD algorithm. The medical images are then viewed at a softcopy review workstation 120 that offers CAD-assisted viewing in accordance with one or more of the preferred embodiments described herein. Also coupled to the network 110 is a PACS (Picture Archiving and Communication System) archive 118, generally representing a repository for medical information associated with the medical imaging environment, including both current and archived images, current and archived CAD results, radiology reports for completed cases, and so forth.

As indicated by the presence of the CT acquisition device 106 and the "other" medical imaging device 108, the preferred embodiments described herein are readily applicable for a variety of present or prospective non-mammography medical imaging modalities such as CT, MRI, PET, SPECT, ultrasound, x-ray tomosynthesis, thermography, electrical conductivity-based modalities, and other modalities. Without loss of generality to the other imaging modalities, the preferred embodiments are described hereinbelow in the particularly advantageous context of a mammography environment.

The preferred embodiments described herein are seamlessly layered upon an existing mammography CAD workflow, in which the digital or digitized mammogram images are processed by the CAD processor 112, and in which the mammogram images and their related CAD results are subsequently displayed at the review workstation 120 to a viewer, who makes a clinical determination therefrom. The clinical determination can be in relation to screening, diagnosis, follow-up, or any of a variety of other activities. Notably, the preferred embodiments herein are particularly advantageous in a screening context for which speed, case throughput, and viewer stamina are important factors.

In one preferred embodiment, the review workstation 120 comprises a multi-modality workstation adapted and configured for a mammography environment. In one example, a Sectra IDS5/mx.net dedicated mammography workstation can be used that allows for third-party plug-ins, including plug-ins providing the CAD user interfacing functionalities described herein. Review workstation 120 comprises diagnostic monitors 122a and 122b, an administrative monitor 124, user input devices 126 (e.g., keyboard, mouse, trackball, pointers, etc), and a user interface processor 128. Administrative monitor 124 is used for input and output of a wide variety of information that may be associated with a particular set of medical images (e.g. listings, tables, plots, text descriptions, etc), as well as for system installation, maintenance, updating, and related tasks. Generally speaking, the administrative monitor 124 can be a relatively low-cost monitor as would be found in generic information processing environments. However, the diagnostic monitors 122a-122b should be FDA-approved as having sufficient luminance, contrast, resolution, and other characteristics that qualify them as proper medical image screening and/or diagnosis tools. By way of example and not by way of limitation, typical characteristics of such diagnostic monitors would currently include: a resolution of 2048×2560 (5 megapixels) at a diagonal size of 21.3 inches (54 cm), a height of 16.6 inches (42.2 cm), and a width of 13.3 inches (33.7 cm); a brightness of 700 cd/m$^2$; and a dynamic range of 3061 different shades of gray.

Notably, the medical imaging environment of FIG. 1 is presented by way of example only and is not intended to limit the scope of the preferred embodiments to this particular scenario. By way of example, different combinations of the devices of FIG. 1 can be placed adjacently to each other or integrated into the same hardware boxes without departing from the scope of the preferred embodiments. By way of still further example, the network 110 can be a wide-area network with the different nodes being distributed throughout a city, a country, or the world. Alternatively, and by way of still further example, some or all of the transfer of digital information can be achieved by physical transfer of disks, memory sticks, or other digital media devices without departing from the scope of the preferred embodiments. In view of the present disclosure, a person skilled in the art would be able to construct such plug-ins or other software packages capable of achieving the described user interfaces and processing functionalities without undue experimentation, using publicly available programming tools and software development platforms.

Figure 2B:
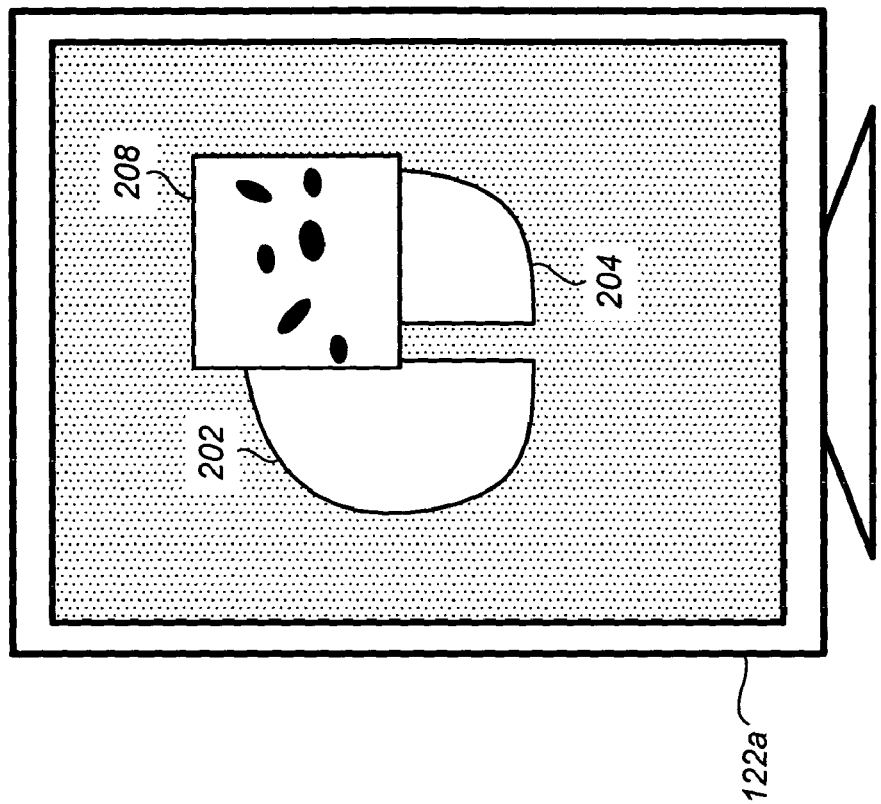
FIGS. 2A and 2B illustrate mammographic image displays including expanded presentation windows according to a preferred embodiment.
Figure 2A:
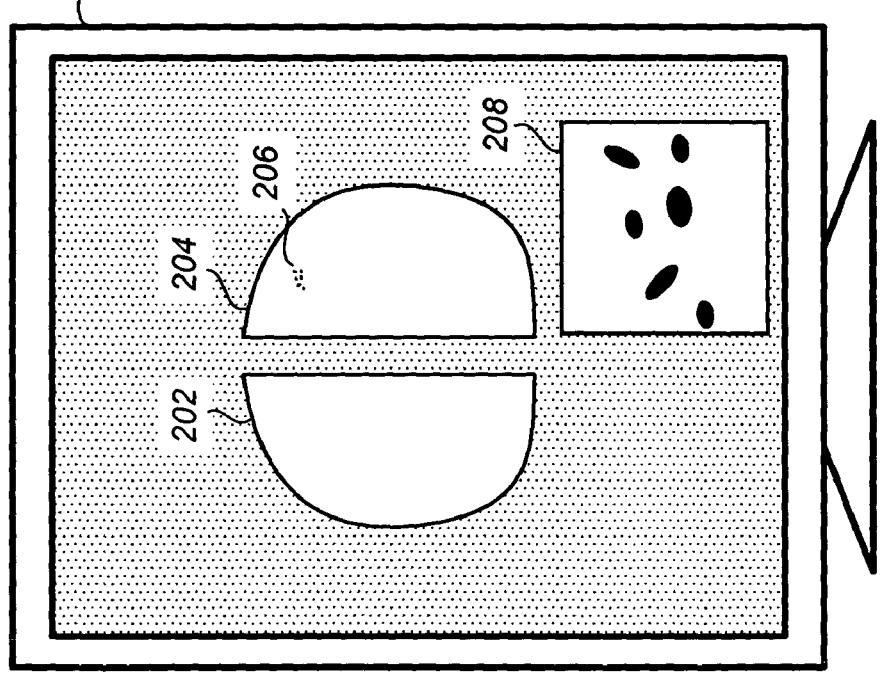

FIGS. 2A-2B each illustrate a mammographic image display including an expanded presentation window according to a preferred embodiment. In FIG. 2A, on the diagnostic monitor 122a is a left portion of a "four-up" display in which there is displayed, from left to right, an RCC view 202, an LCC view 204, an RMLO view (not shown), and an LMLO view (not shown). Corresponding to a CAD-detected lesion 206 (which, by way of non-limiting example, is a microcalcification cluster) is an expanded presentation window 208. In FIG. 2A, the expanded presentation window 208 is positioned adjacent to the RCC/LCC views 202/204 so that all of the tissue is visible in conjunction therewith, while in FIG. 2B the expanded presentation window 208 is superimposed on the LCC view 204 at a location corresponding to the CAD-detected lesion 206.

It is to be appreciated that the various preferred embodiments described herein are not limited to scenarios of dual-diagnostic monitor configurations with four-up displays, but rather includes displays having any number of diagnostic monitors and any of a variety of different hanging protocols with many different combinations of mammographic views present. Accordingly, it is to be appreciated that illustrations or references to single-diagnostic-monitor scenarios can also refer to multiple-diagnostic-display-monitor scenarios, and that illustrations or references to multiple-diagnostic-monitor scenarios can also refer to single-diagnostic-display monitor scenarios. Likewise, illustrations or references to single-mammographic-view scenarios can also refer to multiple-mammographic-view scenarios, and illustrations or references to multiple-mammographic-view scenarios can also refer to single-mammographic-view scenarios.

Expanded presentation window 208, which in one preferred embodiment is similar to a Peerview™ feature developed by R2 Technology, Inc. of Sunnyvale, Calif., provides for close-up viewing of a lesion comparable to the way a conventional magnifying glass would facilitate close-up viewing of a film mammogram on a light box. In a simplest preferred embodiment, the expanded presentation window 208 simply provides a close-up view of the lesion, optionally while also highlighting the pixels of the microcalcifications, masses, spiculations, etc., in non-natural colors such as bright red or yellow, and optionally while also providing variable zoom for the viewer. In other preferred embodiments, the expanded presentation window provides a variety of other helpful tools including, but not limited to, viewer manipulation of tone, interactive viewing of CAD-computed feature characteristics, and interactive segmentation or analysis.

Optionally, the viewer is allowed to click-and-drag the expanded presentation window 208 to any desired position on the screen. The viewer may also specify a "default" setting that dictates whether the expanded presentation window 208 will be adjacent to the images as in FIG. 2A or superimposed over lesion locations as in FIG. 2B when instantiated.

In one preferred embodiment, the expanded presentation window 208 immediately appears upon user instantiation of CAD-assisted viewing (e.g., by pressing a "CAD" or "Show CAD Results" button), without requiring the viewer to first view an overall annotation map and click on a particular one of the displayed CAD markers. It is to be appreciated that the scope of the preferred embodiments can include a first scenario in which all CAD markers are displayed on the RCC/LCC views 202/204 (at locations not occluded by the expanded presentation window 208), and can further include a second scenario in which no CAD markers are displayed on the RCC/LCC views 202/204 when the expanded presentation window is being displayed. The scope of the preferred embodiments can further include a third scenario in which only a single CAD marker is displayed, in particular, the CAD marker corresponding to the currently displayed expanded presentation window 208. In still another preferred embodiment, there can be a viewer choice made among these scenarios, and that choice may be associated with a default profile for each viewer.

Figures 1, 3:
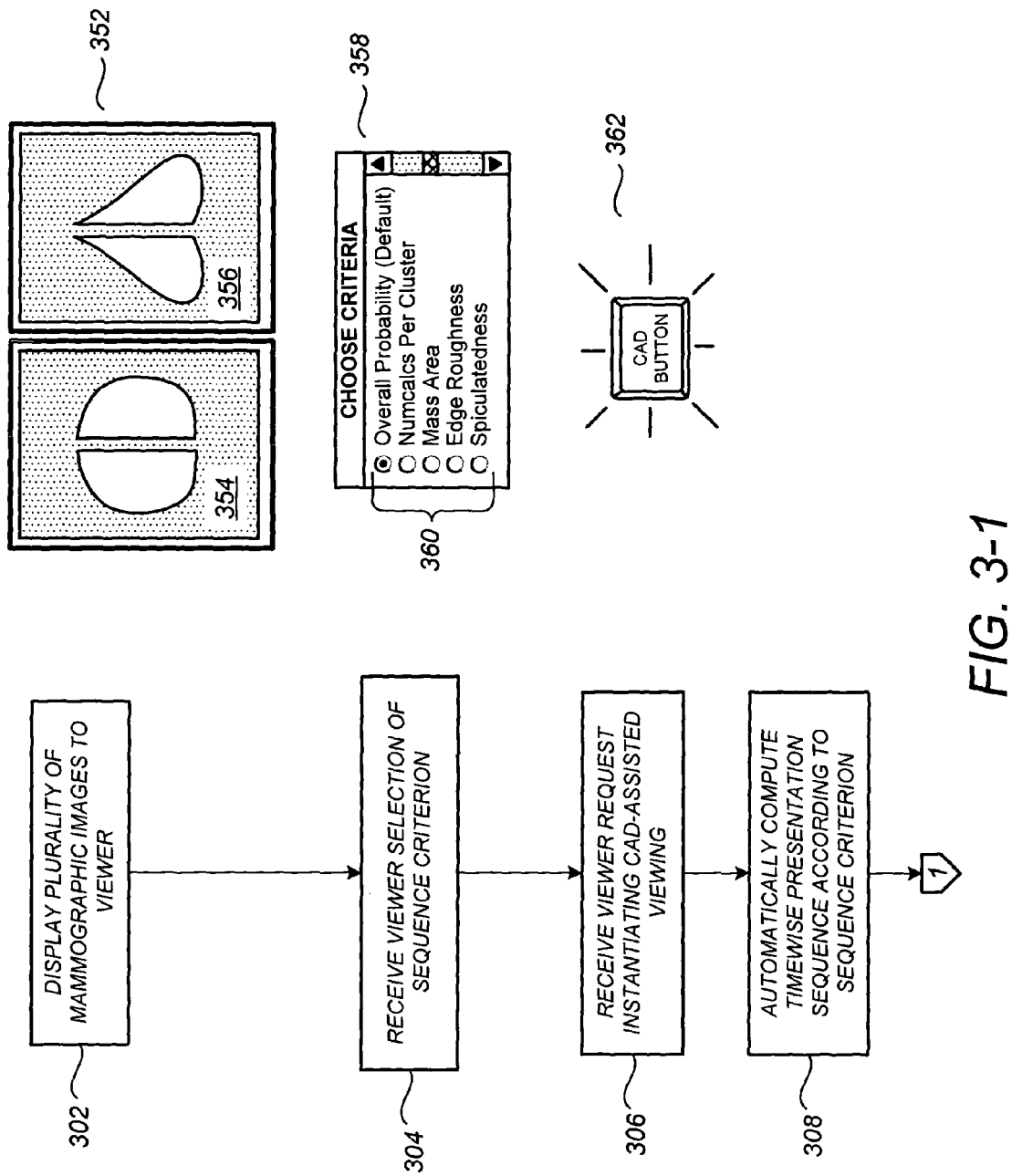
FIG. 3 illustrates displaying CAD results according to a preferred embodiment.
Figures 2, 3:
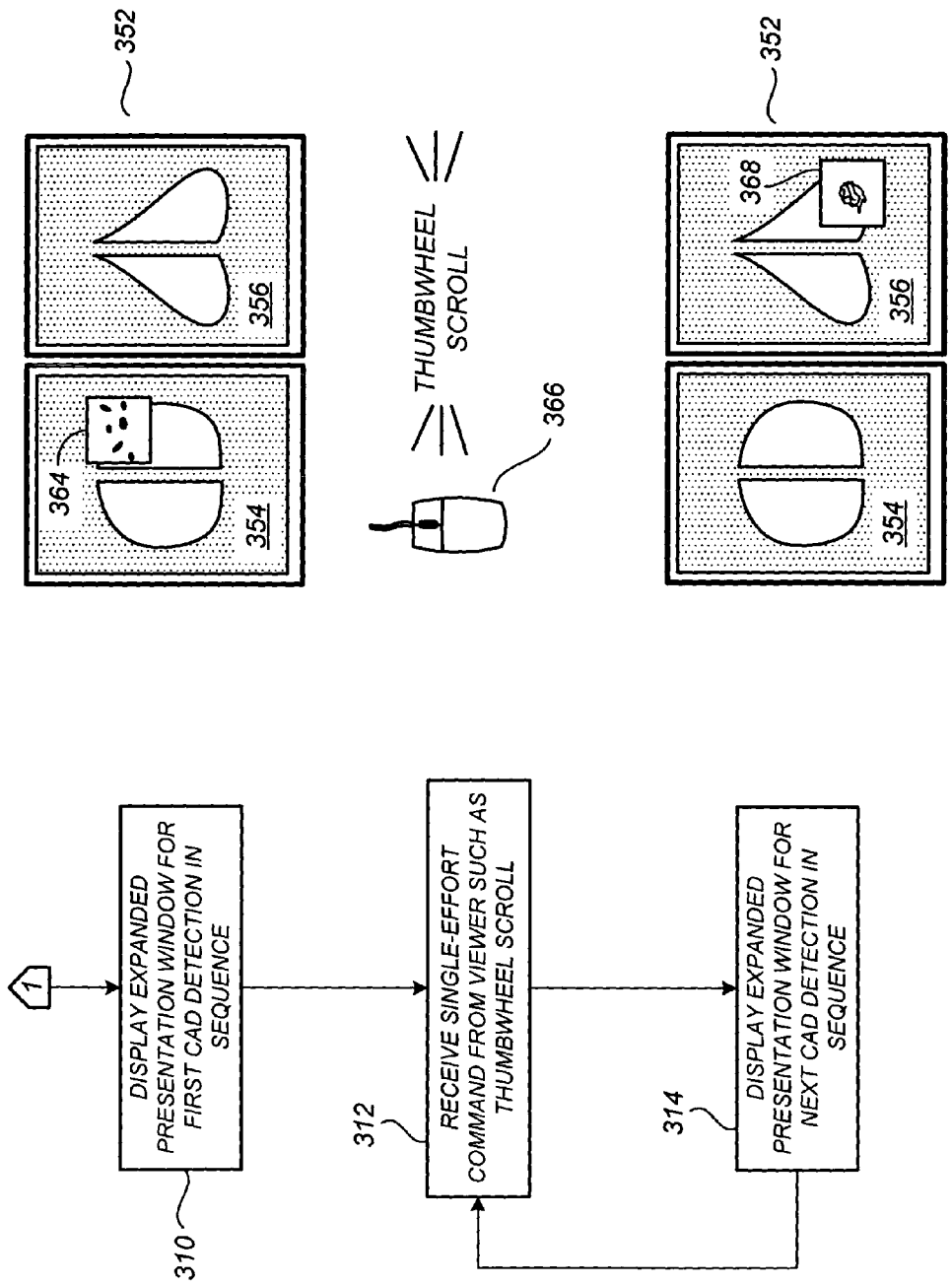

FIG. 3 illustrates displaying CAD results according to a preferred embodiment, with certain drawings being included next to certain blocks of FIG. 3 for clarity of presentation. At step 302, a plurality of mammographic images is displayed to a viewer, such as images 354/356 on a diagnostic monitor(s) 352. Usually, the CAD processing for these mammographic images will have already taken place, although the scope of the preferred embodiments is not so limited. At step 304, viewer selection of a sequencing criterion is received, such as through use of a selection box 358 having selectable radio buttons for differing choices. In one preferred embodiment, the sequencing criterion can comprise one of a plurality of computed features associated with the CAD algorithm. In other preferred embodiments, the sequencing criterion can comprise combinations of different computed features as weighted according to the viewer's desires, or according to a predefined profile for the viewer and/or clinic. Accordingly, it is to be appreciated that the term sequencing criterion, which is singular in referring to the ultimate choice of rules by which CAD detections will be sequenced for presentation to a particular viewer for a particular case, is not limited to singular computed features, but rather can be a combination of different criteria incorporating different computed features. Many different sequencing criteria may be offered to the viewer, such as overall probability of suspiciousness, number of calcifications per cluster, mass area, edge roughness, spiculatedness, etc.

At step 306, a viewer request is received for instantiating CAD-assisted viewing. By way of example, FIG. 3 illustrates a "CAD BUTTON" 362 for receiving this command. At step 308, a timewise presentation sequence is automatically computed according to the sequencing criterion. Usually, the computed features used in determining the sequence of presentation will have already been precomputed by the CAD algorithm, but the scope of the preferred embodiments is not so limited. For example, it may be the case that a particular sequencing criterion desirable for a particular viewer may be a formula involving different features computed by the CAD algorithm. That particular formula for that particular viewer might not have been needed by the CAD algorithm in arriving at its CAD detections, but would still be considered a computed feature as that term is used herein. Accordingly, it may be the case that one or more computed features will be computed on-the-fly at the review workstation 120 and will not have been pre-computed by the CAD algorithm.

Although a variety of different sequencing criteria may be offered and selected, one particularly useful criterion is an overall suspiciousness metric as computed by the CAD algorithm. While differing CAD algorithms will often have different nomenclatures and scalings, there is often an "ultimate" or "overall" scalar score assigned to each candidate detection associated with its likelihood of being a true lesion, or a malignant cancer. For cases having multiple CAD detections, it has been found valuable to sequence the corresponding expanded presentation windows according to the overall suspiciousness metric. Preferably, they are in an order such that the "most problematic" lesion is shown first, followed by the next-most-problematic lesion, and so on, according to the overall suspiciousness metric. In this manner, viewer expectation and viewer attention may systematically interact in a manner that increases viewer stamina and/or increases the quality of review. In one preferred embodiment indicated by selection box 358 of FIG. 3, the sequencing criterion is set to the overall suspiciousness metric by default, although it can be overridden by viewer choice.

At step 310, an expanded presentation window is displayed for the first CAD detection in the computed sequence (see window 364). At step 312, a single-effort command is received from the viewer such as a scrolling of a thumbwheel of a mouse 366 or the pressing of a single "next" button or the like. In the event of a button, it is preferred that it be a physical button rather than a softbutton so that mouse aiming, which takes some physical effort, is not required, although the scope of the preferred embodiments is not so limited. At step 314, an expanded presentation window is displayed for the second CAD detection in the computed sequence (see window 368), and the steps 312-314 are repeated for the third CAD detection in the sequence, fourth CAD detection, etc.

For each step through successive expanded presentation windows, the viewer may optionally elect to interact with that window without departing from the scope of the preferred embodiments. The steps of FIG. 3 subsequent to step 302 may be accompanied, in one scenario, with a showing of all of the CAD markers at their respective locations on the displayed mammograms (if not occluded by an expanded presentation window) or, in another scenario, with no CAD markers being displayed. In another scenario, a viewer-defined default setting determines whether CAD markers will, or will not, be displayed in conjunction with the sequence of expanded presentation windows.

Figure 4:
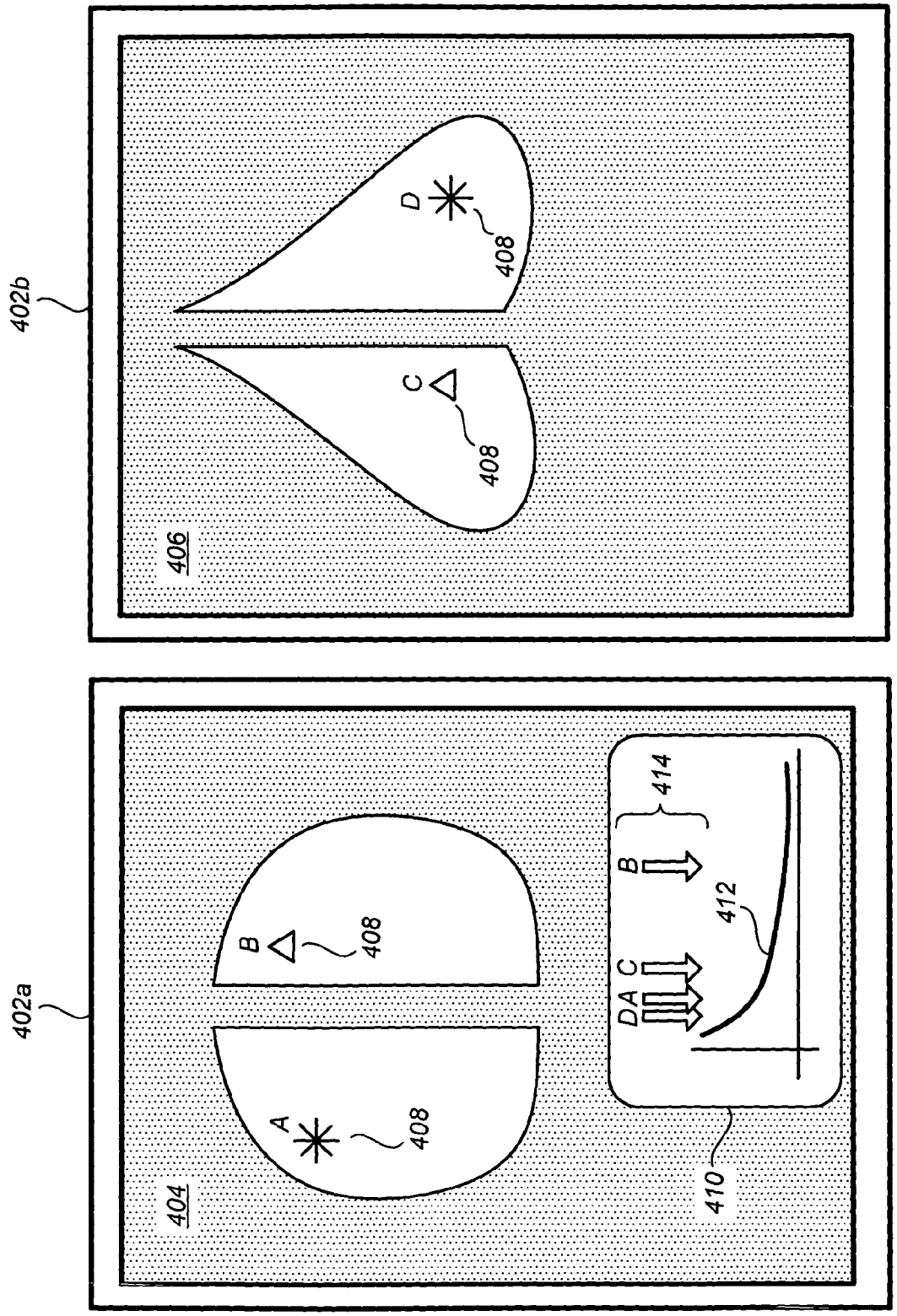
FIG. 4 illustrates a workstation display including a navigational tool according to a preferred embodiment.

FIG. 4 illustrates a workstation display according to a preferred embodiment, in which CC views 404 and MLO views 406 are displayed on diagnostic monitors 402a and 402b, respectively, and in which a navigational tool 410 is displayed. CAD markers 408 are provided at locations corresponding to CAD detections as detected by a CAD algorithm, the CAD markers 408 having designations A, B, C, and D for purposes of the present description. The navigational tool 410 comprises an operating curve 412 and a plurality of CAD pointer icons 414, each CAD pointer icon 414 corresponding to a respective one of the CAD markers 408 and having a corresponding designation A, B, C, or D. Whereas each CAD marker 408 is a graphical annotation representing a particular location of a CAD detection (and possibly other characteristics of that CAD detection), each CAD pointer icon 414 is a graphical symbol that points to, or represents the existence of, one of the CAD detections, but is not in itself a CAD marker. In a sense, each CAD pointer icon 414 can be thought of as a "meta-marker" that, although not visually communicating a location of a CAD detection, serves to visually communicate some other aspect of a CAD detection by virtue of its position on the display and/or by its graphical appearance.

In the preferred embodiment of FIG. 4, visual correspondence between the CAD pointer icons 414 and the CAD markers 408 is alphanumeric, i.e., using the characters A, B, C, and D. In other preferred embodiments, this visual correspondence can be established using color, i.e., using a different color for each marker-pointer icon pair. In still other preferred embodiments, correspondence can be based on size, flashing characteristic, shape, or other characteristic. One particularly useful method is to have two-way rollover correspondence between the CAD markers and the CAD pointer icons, i.e., if the mouse cursor is rolled over one of the CAD markers, then the corresponding CAD pointer icon brightens up, and vice-versa.

As will be described in further detail below, the operating curve 412 is a plot onto which a particular computed feature associated with the CAD algorithm can be mapped, and characterizes an application of the CAD algorithm to a reference database of mammographic cases having known diagnoses. The CAD pointer icons 414 are spatially distributed along the navigational tool 410 according to mappings of that particular computed feature onto the operating curve. Accordingly, viewer perception of the plurality of CAD detections relative to each other and to the reference database with respect to that particular computed feature is facilitated upon a quick viewing of the navigational tool 410. In one preferred embodiment, the particular computed feature is the overall suspiciousness metric described supra. In another preferred embodiment, the particular computed feature can be user-selected according to the selection box 358 of FIG. 3, supra, or any combination of such computed features. Without loss of generality, a preferred embodiment in which the particular computed feature is the overall suspiciousness metric is described hereinbelow.

For many CAD algorithms, the overall suspiciousness metric is thresholded during the CAD algorithm in determining whether candidate detections will qualify as marked "detections." FIG. 5 illustrates a thresholding rule 502 in a CAD algorithm according to a preferred embodiment, in which PCAD denotes is the overall suspiciousness metric. In operation according to the thresholding rule 502, the CAD algorithm makes a binary decision based on PCAD, and in particular qualifies a candidate detection to be a "detection" if PCAD is greater than a threshold value MT (marking threshold) and a "non-detection" otherwise. Notably, in many CAD algorithms, there may be subsequent "cuts" of markers after such thresholding (e.g., due to a predetermined maximum number of markers per view, per lesion category, or per case), so the thresholding process would represent a necessary, but not always sufficient, condition for a candidate detection to become a marked "detection."

FIGS. 6-9 illustrate operating curves of a navigational tool according to one or more of the preferred embodiments reflecting the application of the CAD algorithm to the reference database of known mammographic cases. The reference database may similar to that described in 2001/0043729A1, supra. The reference database may be a local database for a particular clinic, a proprietary database for a particular CAD software provider, a regional or national public database, etc. The reference database may be dynamically updated for a particular clinic (or CAD company, or region, nation, etc.) as diagnoses for mammographic cases become known (e.g., known "benign" versus known "malignant"), and may further store follow-up information, biopsy methods/results, and the like. According to a preferred embodiment, the CAD algorithm for which the navigational tool 410 will be shown is caused to operate on all of the images in the reference database and to generate computed features therefrom. A variety of operating curves characterizing the application of the CAD algorithm to the reference database become available including, but not limited to, various receiver operating characteristics, histograms of computed feature values, sensitivity and specificity curves, and the like.

FIG. 6 illustrates a plot of an operating curve 602 according to one preferred embodiment including, on the abscissa or horizontal axis 606, a range of values for the marking threshold MT from a minimum value to a maximum value of $PCAD_{MAX}$ and, on the ordinate or vertical axis, the number of cancers in the reference database when the different marking thresholds MT are used. As the value of MT increases, the number of cancers detected decreases because the overall suspicious metric PCAD needs to be higher and higher for the candidate detection to qualify as a "detection" by the CAD algorithm. The operating curve 602 represents a plot onto which a particular computed feature PCAD can be mapped. For any particular value PCAD, the operating curve 602 represents a performance characteristic (number of cancer detections or percent of cancer detections) that the CAD algorithm would provide for the reference database if the marking threshold MT were set to the value PCAD.

FIG. 7 illustrates a plot of an operating curve 702 according to another preferred embodiment that plots false marks per case (FMPC) on the abscissa and the number of known cancers detected in the reference database on the ordinate. The operating curve 702 characterizes an application of the CAD algorithm to the reference database. The operating curve 702 is also a plot onto which a particular computed feature, PCAD, associated with the CAD algorithm can be mapped. In this case, PCAD can be mapped parametrically on the operating curve 702, with each differing threshold value $MT=PCAD_x$ corresponding to a different operating point.

Referring now back to FIG. 4, it can be readily seen that a prompt comparison can be drawn among the various CAD detections with respect to each other, and with respect to the reference database of known cases, by viewing the navigational tool 410. Where the abscissa of the plot is similar to those in FIGS. 6-7, the horizontal positioning immediately communicates (i) that lesion "B" is more troublesome than lesions A, C, and D, and (ii) that lesion "B" is also quite troublesome relative to the reference database of known cases, in terms of overall suspiciousness. Thus, the navigational tool 410 conveys a great deal of valuable information that a radiologist would find useful. It shows essentially in a global manner how this CAD detection compares with "all" other lesions—i.e., close to the majority, or near the threshold with very subtle lesions. The graphic also shows the position of the CAD detection relative to the others in the case—showing for example which are the most important, prominent, conspicuous lesions (those on the left hand of the x axis) and which less (to the right). It is to be appreciated that the x-axis of the navigational tool 410 can be oriented differently, e.g., at a 90-degree angle or at a different angle, without departing from the scope of the preferred embodiments.

Figure 8:
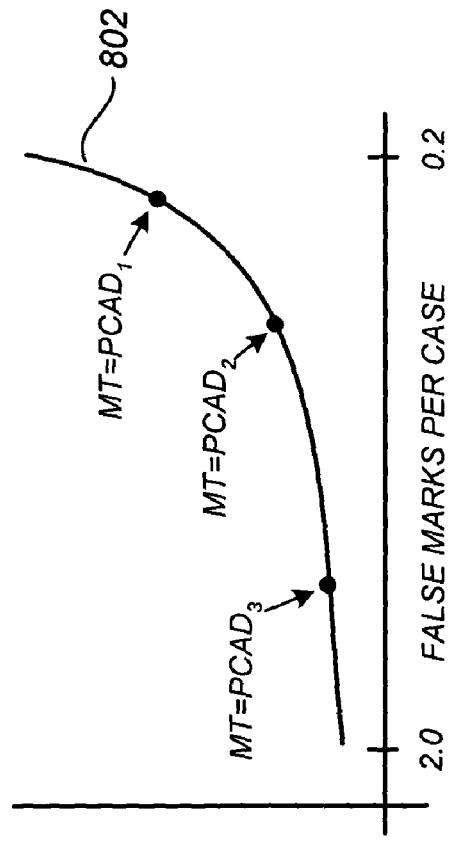
Figure 9:
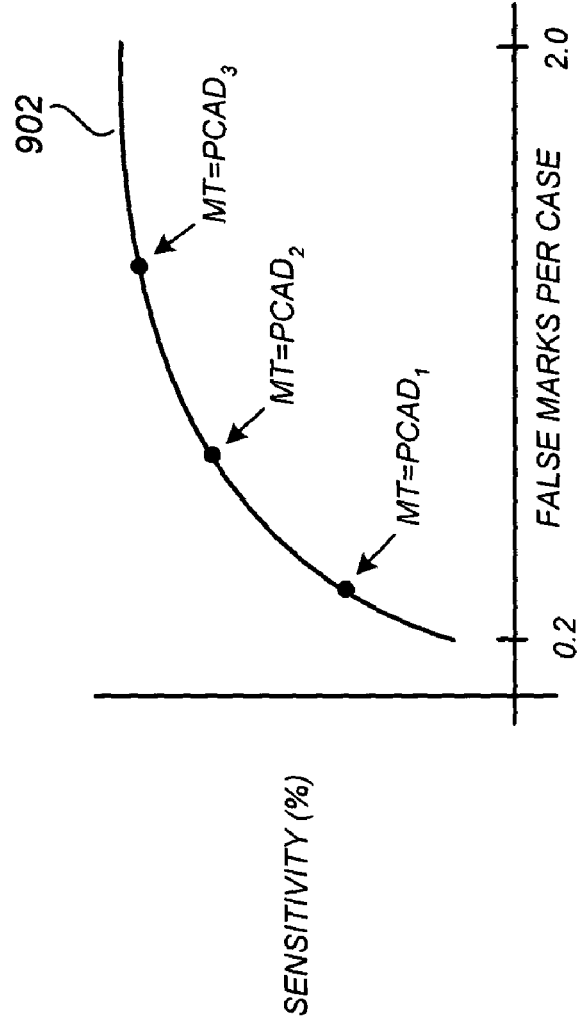

FIGS. 8-9 illustrate examples of other operating curves that may be used in a navigational tool according to a preferred embodiment. Operating curve 802 of FIG. 8 is the same as operating curve 702 of FIG. 7 with the abscissa reversed, which may have more intrinsic familiarity to some practitioners depending on training and geography, for example. Operating curve 902 of FIG. 9 is a sensitivity plot versus false marks per case (FMPC), otherwise referred to as an FROC (free receiver operating characteristic) curve that many practitioners are particularly comfortable with. The operating curves 802/902 are plots onto which a particular computed feature associated with the CAD algorithm, PCAD, can be mapped.

Figure 10:
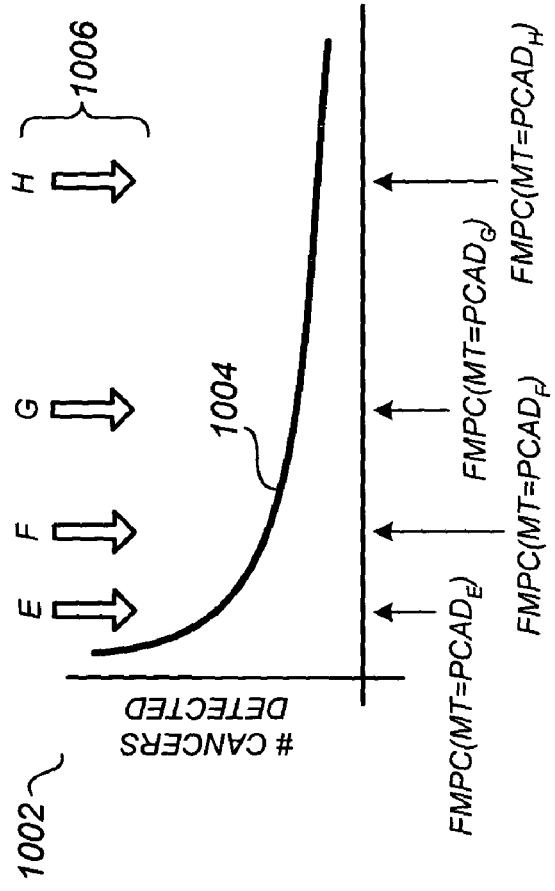
FIG. 10 illustrates a navigational tool according to a preferred embodiment.

FIG. 10 illustrates a navigational tool 1002 according to a preferred embodiment, comprising an operating curve 1004 similar to the operating curve 702 of FIG. 7, and further comprising CAD pointer icons 1006. To generate the navigational tool 1002 of FIG. 10, the following steps can be performed: (i) identify a suitable operating curve characterizing the application of the CAD algorithm to the reference database (in this example, number of known cancers detected versus FMPC (false marks per case)); (ii) identify the computed feature that is of interest (in this example, overall suspiciousness PCAD), (iii) for each CAD detection, extract the value for that computed feature ($PCAD_x$), and (iv) for each CAD detection, map that computed feature value $PCAD_x$ onto the operating curve by identifying the abscissa FMPC ($MT=PCAD_x$) associated therewith, and place a CAD pointer icon along that abscissa location in general proximity to the operating curve.

Figure 11:
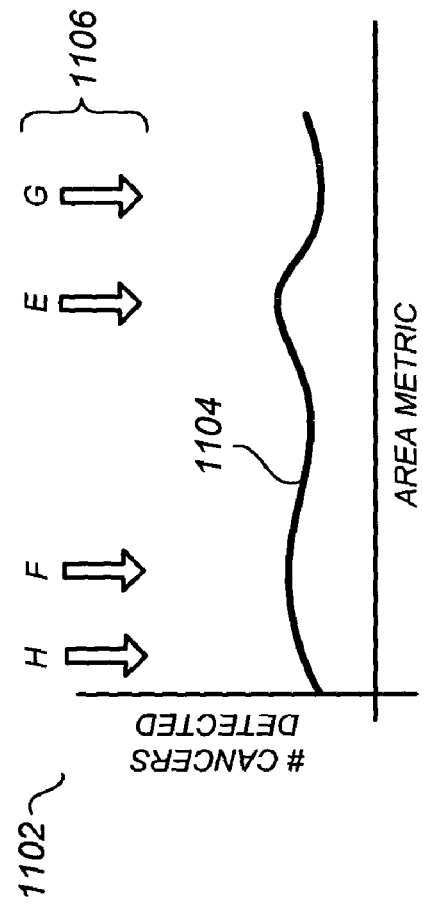
FIG. 11 illustrates a navigational tool according to a preferred embodiment.

FIG. 11 illustrates a navigational tool 1102 according to a preferred embodiment, comprising an operating curve 1104 characterizing the application of the CAD algorithm to the reference database with respect to a particular parameter, in this case an area metric. In this example, the operating curve 1104 is simply a histogram of the number of known cancers detected in the reference database having each particular range of computed area values, and the CAD pointer icons 1106 are positioned thereon at positions corresponding to the area metric for the corresponding CAD detections.

FIG. 12 illustrates navigating CAD results using the navigational tool 410 according to a preferred embodiment as applied to the CC/MLO views 404/406 of FIG. 4. According to a preferred embodiment, for an even richer and concise review experience, the same criterion is used for both (i) the positioning of CAD pointer icons on the navigational tool 410, and (ii) navigation among expanded presentation windows on the mammographic images. Thus, in a first frame FIG. 12 shows the CAD detection "B" having a highlighted CAD pointer icon, and also having an expanded presentation window 1202 displayed over the corresponding location. After a single-effort command such as a mouse wheel scroll, a second frame shows the CAD detection "C" having a highlighted CAD pointer icon and an expanded presentation window 1204 at the relevant location. After another single-effort command, a third frame shows the CAD detection "A" having a highlighted CAD pointer icon and an expanded presentation window 1206, and after another single-effort command, a fourth frame shows the CAD detection "D" having a highlighted CAD pointer icon and an expanded presentation window 1208 at the relevant location. At any time, the viewer is permitted to depart from the sequence by clicking on a particular CAD pointer icon or on a particular CAD marker (if CAD markers are being displayed), in which case the corresponding expanded presentation window for that CAD pointer icon or CAD marker is displayed.

Figure 13:
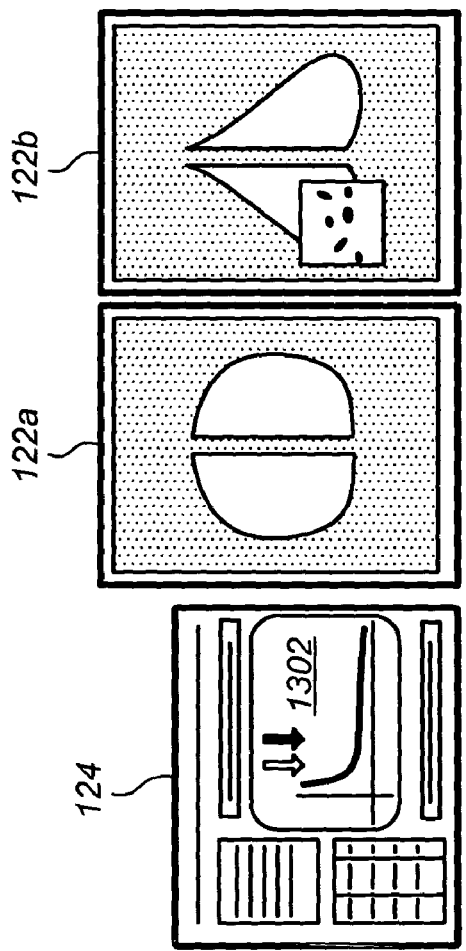
FIG. 13 illustrates a navigational tool positioned with a four-up mammographic display according to a preferred embodiment.
Figure 14:
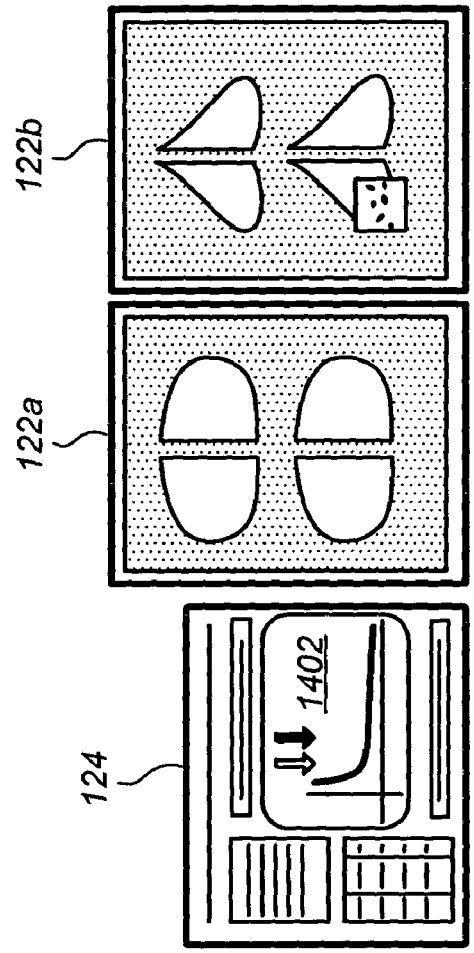
FIG. 14 illustrates a navigational tool positioned with an eight-up mammographic display according to a preferred embodiment.

FIG. 13 illustrates a navigational tool 1302 positioned with a four-up mammographic display according to a preferred embodiment, while FIG. 14 illustrates a navigational tool 1402 positioned with an eight-up mammographic display according to a preferred embodiment. In these examples, and with reference to FIG. 1, supra, the navigational tools are displayed on the administrative monitor 124 rather than on the diagnostic monitors 122a/122b, which can be an advantageous way to save "real estate" on the display when it becomes scarce due to the number of images simultaneously displayed in the currently chosen hanging protocol.

Thus, in accordance with one or more advantages according to the preferred embodiments, there is provided at least one of (i) a timewise dimension, and (ii) a visual spatial dimension for prompt comparative viewing of multiple CAD detections in a case. Additionally, there is concurrently provided a prompt comparison of the multiple CAD detections with a reference database of known cases. An advantageous combination of quickness and richness of analysis is provided that promotes one or more of faster patient throughput, viewer stamina, reduced per-patient cost, and increased quality of review.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, it is to be appreciated that while the preferred embodiment of FIG. 4 illustrates CAD markers 408, in other preferred embodiments the CAD markers 408 can be omitted except for a marker corresponding to the currently displayed expanded presentation window. In other preferred embodiments there can be a viewer choice whether the CAD markers 408 are displayed as the viewer proceeds through the presentation sequence of CAD detections.

By way of further example, in other preferred embodiments a plurality of expanded presentation windows can be simultaneously displayed, which can be particularly advantageous for correlated CAD markers/detections. As known in the art (see, e.g., U.S. Pat. No. 6,075,879, supra), many CAD algorithms attempt to establish a correlation between CAD detections in one view of a breast with CAD detections in a different view of that same breast, to determine whether two CAD detections (for example, one in the LCC view and another in the LMLO view) might actually correspond to the same physical lesion in the breast. In such case, the overall suspiciousness metric for both CAD detections would be raised. In accordance with one preferred embodiment, if correlated CAD detections are encountered as the viewer progresses through the sequence of expanded presentation windows, dual expanded presentation windows (one for each CAD detection) are automatically displayed in their respective mammographic views.

In still other preferred embodiments, there can be one expanded presentation window that is constantly displayed per mammographic view, for example, in a "permanent" expanded presentation window frame for each mammographic view. In such case, the "current" expanded presentation window associated with a currently selected CAD marker or CAD pointer icon would be highlighted relative to the other expanded presentation windows in the case. Optionally, upon viewer instantiation of CAD-assisted viewing, the expanded presentation window for each mammographic view would immediately display the most suspicious CAD detection for that view. In yet another preferred embodiment, the methods described supra with respect to FIGS. 3 and 4 can be separately executed for each mammographic view, with each mammographic view having its own presentation sequence and/or its own navigational tool. Such preferred embodiment would likely be more useful for imaging modalities that set forth a large number of false positives.

In still other preferred embodiments, the operating curves can represent hypothetical applications of the CAD algorithm to hypothetical "generic" populations, in which case they might be selected and designed by the CAD algorithm provider or other radiology experts to yield meaningful bases for visual comparisons while not actually having been run for an actual population of patients. In still other preferred embodiments, the plot of the operating curve can take the form of a linear color-coded graph or intensity plot. In such cases, the plots would have a single axis along the abscissa, and the ordinate dimension would be expressed as a color or an intensity distribution along the linear graph. Therefore, reference to the details of the preferred embodiments are not intended to limit their scope, which is limited only by the scope of the claims set forth below.

What is claimed is:

1. A method for displaying a mammogram and graphical information relating to a plurality of CAD detections associated the mammogram as detected by a CAD algorithm, each CAD detection corresponding to a detected anatomical abnormality as detected by the CAD algorithm, comprising:

displaying the mammogram to a viewer on a user display, including superimposing CAD annotation markers thereon corresponding respectively to said plurality of CAD detections associated therewith, each CAD annotation marker being superimposed on the displayed mammogram at a location of its corresponding detected anatomical abnormality; and simultaneously with said displaying the mammogram, displaying a graphical tool spatially distinct from said mammogram on the user display in general proximity to the mammogram to allow simultaneous viewing of the mammogram and said graphical tool, said graphical tool comprising:

a plot of an operating curve onto which a first computed feature associated with the CAD algorithm can be mapped, the operating curve characterizing an application of the CAD algorithm to a reference database of mammographic cases having known diagnoses, each of said CAD detections having an assigned value for said first computed feature as computed by said CAD algorithm; and a plurality of CAD pointer icons, each said CAD pointer icon corresponding to a respective one of the CAD detections, each said CAD pointer icon being spatially positioned on said graphical tool according to a mapping of said assigned first computed feature value of its corresponding CAD detection onto said operating curve;

each said CAD detection thereby being graphically characterized on the user display by virtue of a combination of (i) said location of the corresponding CAD annotation marker relative to said mammogram, and (ii) said position of the corresponding CAD pointer icon relative to said operating curve;

whereby viewer perception of said plurality of CAD detections relative to each other and to said reference database with respect to said first computed feature characteristic is facilitated.

2. The method of claim 1, wherein said first computed feature comprises a scalar overall probability metric thresholded by the CAD algorithm for qualifying candidate detections as becoming "detections" versus "non-detections", wherein an abscissa of said operating curve comprises a false marks per case metric, and wherein an ordinate of said operating curve comprises a metric proportional to a number of cancers detected by said CAD algorithm in said reference database when operating at said false marks per case metric.

3. The method of claim 1, wherein an abscissa of said operating curve comprises said first computed feature, and wherein an ordinate of said operating curve comprises a metric for number of cancers detected by said CAD algorithm in said reference database having said first computed feature value.

4. The method of claim 1, wherein said operative curve is represented by one of a two-dimensional graph, a linear color-coded graph, and a linear intensity-coded graph.

5. The method of claim 1, wherein said operating curve comprises a histogram of a number of cancers detected in the reference database by the CAD algorithm at each possible value of said first computed feature.

6. The method of claim 1, wherein said operating curve comprises a receiver operating characteristic for said CAD algorithm as applied to said reference database.

7. The method of claim 1, each CAD detection being associated with a location in the mammogram, further comprising:

receiving a viewer selection of one of said CAD pointer icons;

responsive to said viewer selection, displaying an expanded presentation window for the location in the mammogram associated with the CAD detection corresponding to the selected CAD pointer icon.

8. The method of claim 1, each CAD detection being associated with a location in the mammogram, further comprising:

automatically computing a timewise presentation sequence for said CAD detections according to a predetermined sequencing criterion; and for each CAD detection, displaying an expanded presentation window for its associated location in the mammogram;

wherein said expanded presentation windows are sequentially displayed according to said computed timewise presentation sequence for said CAD detections.

9. The method of claim 8, wherein each of said expanded presentation windows is superimposed upon said mammogram at the location associated with that CAD detection.

10. The method of claim 9, wherein each of said expanded presentation windows allows for at least one of (i) viewer manipulation of scale, (ii) viewer manipulation of tone, (iii) interactive viewing of CAD-computed feature characteristics, and (iv) interactive segmentation or analysis.

11. The method of claim 8, wherein said timewise presentation sequence for said CAD detections corresponds to said spatial distribution of said CAD pointer icons along said graphical tool.

12. The method of claim 11, wherein said first computed feature is viewer-selectable.

13. The method of claim 11, further comprising allowing the viewer to manually step through said sequence of expanded presentation windows using a single-effort input command.

14. The method of claim 13, wherein said single-effort input command comprises one of (i) scrolling a mouse wheel, and (ii) pressing a single button.

15. The method of claim 13, wherein any CAD pointer icons on said graphical tool corresponding to CAD detections not currently viewable in the mammogram are ghosted relative to the other CAD pointer icons, and wherein the CAD pointer icon corresponding to a currently displayed expanded presentation window is highlighted relative to the other CAD pointer icons.

16. A computer program product stored on a non-transitory tangible storage medium for directing a medical softcopy workstation to display graphical information relating to a plurality of CAD detections associated with a medical image of a body part as detected by a CAD algorithm, each CAD detection corresponding to a detected anatomical abnormality as detected by the CAD algorithm, comprising:

computer code for displaying the medical image to a viewer on a user display of the medical softcopy workstation;

computer code for receiving a request from the viewer to instantiate CAD-assisted viewing of the medical image;

computer code for superimposing CAD annotation markers on the medical image corresponding respectively to said plurality of CAD detections associated therewith, each CAD annotation marker being superimposed on the displayed medical image at a location of its corresponding detected anatomical abnormality;

computer code for displaying a navigational tool spatially distinct from said medical image on the user display in general proximity to the medical image to allow simultaneous viewing of the medical image and said navigation tool, said navigational tool comprising:

a plot of an operating curve onto which a first computed feature associated with the CAD algorithm can be mapped, the operating curve characterizing an application of the CAD algorithm to a reference database of medical images of the body part having known diagnoses, each of said CAD detections having an assigned value for said first computed feature as computed by said CAD algorithm; and a plurality of CAD pointer icons, each said CAD pointer icon corresponding to a respective one of the CAD detections, each said CAD pointer icon being spatially positioned on said navigational tool according to a mapping of said assigned first computed feature value of said corresponding CAD detection onto said operating curve;

each said CAD detection thereby being graphically characterized on the user display by virtue of a combination of (i) said location of the corresponding CAD annotation marker relative to said medical image, and (ii) said position of the corresponding CAD pointer icon relative to said operating curve;

whereby viewer perception of said plurality of CAD detections relative to each other and to said reference database with respect to said first computed feature characteristic is facilitated;

and computer code for displaying, for each CAD detection, an expanded presentation window for its associated location in the medical image, said expanded presentation windows being sequentially displayed according to the spatial positions of the corresponding CAD pointer icons in said navigational tool.

17. The computer program product of claim 16, wherein said first computed feature comprises a scalar overall probability metric that, as part of said CAD algorithm, is thresholded for qualifying candidate detections as becoming "detections" versus "non-detections".

18. The computer program product of claim 16, wherein said first computed feature is viewer-selectable.

19. The computer program product of claim 18, further comprising computer code for allowing the viewer to manually step through said sequence of expanded presentation windows using a single-effort input command.

20. The computer program product of claim 19, wherein said single-effort input command comprises one of (i) scrolling a mouse wheel, and (ii) pressing a single button.

21. The computer program product of claim 16, wherein said first computed feature comprises a scalar overall probability metric thresholded by the CAD algorithm for qualifying candidate detections as becoming "detections" versus "non-detections", wherein an abscissa of said operating curve comprises a false marks per case metric, and wherein an ordinate of said operating curve comprises a metric proportional to a number of cancers detected by said CAD algorithm in said reference database when operating at said false marks per case metric.

22. The computer program product of claim 16, wherein an abscissa of said operating curve comprises said first computed feature, and wherein an ordinate of said operating curve comprises a metric for number of cancers detected by said CAD algorithm in said reference database having said first computed feature value.

23. The computer program product of claim 16, wherein said plot of said operating curve comprises one of a two-dimensional graph, a linear color-coded graph, and a linear intensity-coded graph.

24. The computer program product of claim 16, wherein said operating curve comprises a histogram of a number of cancers detected in the reference database by the CAD algorithm at each possible value of said first computed feature.

25. The computer program product of claim 16, wherein said operating curve comprises a receiver operating characteristic for said CAD algorithm as applied to said reference database.

* * * * *